(12) United States Patent  (10) Patent No.: US 9,011,684 B2
Kyle  (45) Date of Patent: Apr. 21, 2015

(54) FLUID CONCENTRATOR WITH REMOVABLE CARTRIDGE

(75) Inventor: Matthew R. Kyle, Wayzata, MN (US)

(73) Assignee: SpineSmith Holdings, LLC, Austin, TX (US)

( * ) Notice: Subject to any disclaimer, the term of this patent is extended or adjusted under 35 U.S.C. 154(b) by 950 days.

(21) Appl. No.: 13/041,962

(22) Filed: Mar. 7, 2011

(65) Prior Publication Data

US 2012/0231529 A1  Sep. 13, 2012

(51) Int. Cl.
*B01D 35/30* (2006.01)
*B01D 35/157* (2006.01)
*C12M 1/00* (2006.01)

(52) U.S. Cl.
CPC .............. *C12M 45/04* (2013.01); *B01D 35/157* (2013.01)

(58) Field of Classification Search
None
See application file for complete search history.

(56) References Cited

U.S. PATENT DOCUMENTS

| | | | |
|---|---|---|---|
| 3,669,879 A | 6/1972 | Berriman | |
| 4,230,564 A | 10/1980 | Keefer | |
| 4,327,177 A | 4/1982 | Shrimpton | |
| 4,886,597 A | 12/1989 | Wild et al. | |
| 5,078,864 A * | 1/1992 | Whittier | 210/137 |
| 5,165,938 A | 11/1992 | Knighton | |
| 5,405,607 A | 4/1995 | Epstein | |
| 5,663,051 A | 9/1997 | Vlasselaer | |
| 5,674,394 A | 10/1997 | Whitmore | |
| 5,733,545 A | 3/1998 | Hood, III | |
| 5,788,662 A | 8/1998 | Antanavich et al. | |
| 5,840,502 A | 11/1998 | Van Vlasselaer | |
| 5,876,321 A | 3/1999 | Hlavinka et al. | |
| 5,879,280 A | 3/1999 | Hlavinka et al. | |
| 5,891,347 A | 4/1999 | Matsumoto | |
| 5,935,437 A | 8/1999 | Whitmore | |
| 6,001,259 A | 12/1999 | Whitmore | |
| 6,010,627 A | 1/2000 | Hood, III | |
| 6,027,655 A | 2/2000 | Holm | |
| 6,063,297 A | 5/2000 | Antanavich et al. | |
| 6,071,422 A | 6/2000 | Hlavinka et al. | |
| 6,106,727 A | 8/2000 | Krasnoff et al. | |

(Continued)

FOREIGN PATENT DOCUMENTS

EP  1 057 534 A1  12/2000
WO  WO 2005/094914  10/2005

OTHER PUBLICATIONS

Cell Factor Technologies, Inc., 2004, GPS Platelet Concentration System, 10 pages.

(Continued)

*Primary Examiner* — Krishnan S Menon
(74) *Attorney, Agent, or Firm* — Winstead PC

(57) ABSTRACT

A fluid concentrator includes a main housing and a cartridge removably engaged to the main housing. The main housing includes a first end portion having a first port and a second port, an oppositely disposed second end portion and a separation chamber that extends between the first and second end portions. The second end portion has an inlet port and defines a cartridge passage that extends through the second end portion. The separation chamber is in fluid communication with the inlet port. The cartridge includes a first axial end portion that is engaged with the first end portion and an oppositely disposed second axial end portion, a portion of the second axial end portion is disposed in the cartridge passage of the second end portion of the main housing. The cartridge is adapted to filter fluid from the separation chamber.

15 Claims, 19 Drawing Sheets

(56) References Cited

U.S. PATENT DOCUMENTS

| | | | |
|---|---|---|---|
| 6,132,613 A | 10/2000 | Hopkin et al. |
| 6,197,194 B1 | 3/2001 | Whitmore |
| 6,207,066 B1 | 3/2001 | Trese et al. |
| 6,214,338 B1 | 4/2001 | Antanavich et al. |
| 6,299,784 B1 | 10/2001 | Biesel |
| 6,342,157 B1 | 1/2002 | Hood, III |
| 6,354,986 B1 | 3/2002 | Hlavinka et al. |
| 6,398,972 B1 | 6/2002 | Blasetti et al. |
| 6,524,568 B2 | 2/2003 | Worden |
| 6,582,350 B2 | 6/2003 | Dolecek |
| 6,582,386 B2 | 6/2003 | Min et al. |
| 6,596,180 B2 | 7/2003 | Baugh et al. |
| 6,706,008 B2 | 3/2004 | Vishnoi et al. |
| 6,716,187 B1 | 4/2004 | Jorgensen et al. |
| 6,790,371 B2 | 9/2004 | Dolecek |
| 6,793,828 B2 | 9/2004 | Dolecek et al. |
| 6,808,503 B2 | 10/2004 | Farrell et al. |
| 6,855,263 B2 | 2/2005 | Trese et al. |
| 6,884,228 B2 | 4/2005 | Brown et al. |
| 7,077,273 B2 | 7/2006 | Ellsworth et al. |
| 7,223,346 B2 | 5/2007 | Dorian et al. |
| 7,314,460 B2 | 1/2008 | Tu et al. |
| 7,354,515 B2 | 4/2008 | Coull et al. |
| 7,374,678 B2 | 5/2008 | Leach et al. |
| 7,413,652 B2 | 8/2008 | Dolecek et al. |
| 7,452,344 B2 | 11/2008 | Jorgensen et al. |
| 7,470,371 B2 | 12/2008 | Dorian et al. |
| 7,476,312 B2 | 1/2009 | Laing et al. |
| 7,481,941 B2 | 1/2009 | Tsai et al. |
| 7,547,272 B2 | 6/2009 | Ellsworth et al. |
| 7,608,258 B2 | 10/2009 | Mishra |
| 7,694,828 B2 | 4/2010 | Swift et al. |
| 7,695,627 B2 | 4/2010 | Bosch et al. |
| 7,740,760 B2 | 6/2010 | Coull et al. |
| 7,766,900 B2 | 8/2010 | Leach et al. |
| 7,780,860 B2 | 8/2010 | Higgins et al. |
| 7,803,279 B2 | 9/2010 | Coull et al. |
| 7,806,276 B2 | 10/2010 | Leach et al. |
| 7,806,845 B2 | 10/2010 | Arm et al. |
| 7,811,463 B2 | 10/2010 | Dolecek et al. |
| 7,811,607 B2 | 10/2010 | Baugh et al. |
| 7,824,559 B2 | 11/2010 | Dorian et al. |
| 7,833,185 B2 | 11/2010 | Felt et al. |
| 7,838,039 B2 | 11/2010 | Baugh et al. |
| 7,845,499 B2 | 12/2010 | Higgins et al. |
| 7,866,485 B2 | 1/2011 | Dorian et al. |
| 7,867,159 B2 | 1/2011 | Dolecek et al. |
| 7,897,054 B2 | 3/2011 | Dolecek et al. |
| 7,914,689 B2 | 3/2011 | Higgins et al. |
| 7,954,646 B2 | 6/2011 | Leach et al. |
| 8,012,351 B2 | 9/2011 | Coull et al. |
| 2003/0233064 A1 | 12/2003 | Arm et al. |
| 2004/0132003 A1 | 7/2004 | Dolecek et al. |
| 2004/0182795 A1 | 9/2004 | Dorian et al. |
| 2005/0095695 A1 | 5/2005 | Shindler et al. |
| 2005/0184012 A1* | 8/2005 | Coull et al. ........... 210/787 |
| 2006/0060521 A1 | 3/2006 | Harms et al. |
| 2006/0175244 A1 | 8/2006 | Dorian et al. |
| 2008/0108931 A1 | 5/2008 | Bobroff |
| 2008/0166421 A1 | 7/2008 | Buhr et al. |
| 2009/0220482 A1 | 9/2009 | Higgins et al. |
| 2010/0135969 A1 | 6/2010 | Mishra |
| 2010/0260815 A1 | 10/2010 | Kyle et al. |
| 2012/0074073 A1 | 3/2012 | Coull et al. |

OTHER PUBLICATIONS

Harvest Technologies Corp., 2002, Developing Technologies for Accelerating Healing, Naturally, 6 pages.
International Search Report and Written Opinion cited in PCT/US05/13385 mailed Sep. 10, 2008.
Medtronic Biologic Therapeutics & Diagnostics, 2002, Magellan Autologous Platelet Separator, 6 pages.
Osseous Technologies, Inc., Platelet Concentrate Collection System, Instructions for Use, 7 pages (2003).
Spectrum Labs.Com., 2002 "The ABCs of Filtration and Bioprocessing for the Third Millennium", "The ABCs of Filtration".
International Search Report and Written Opinion mailed Sep. 24, 2012.

* cited by examiner

FLUID CONCENTRATOR WITH REMOVABLE CARTRIDGE

BACKGROUND

Concentration of body fluids has long been practiced in the medical arts. Many medical treatments involve applying a fluid or gel-like substance to a wound or disease location. For some medical treatments, a fluid or gel-like substance or cells is obtained from a body fluid or tissue of another person or animal. Body fluids, components of body fluids, or components of other body parts, such as tissue and cells, may also be obtained from other species and used on human patients. Examples of such biological materials which are commonly used in current medical applications on humans are components of mammalian blood and bone, such as allogenic, xenogenic or autogenic graft or cellular materials, including from human, bovine and porcine sources. In some applications, the concentration process is carried out in an ongoing, streaming process, wherein the body fluid, tissue, or cells is removed from the patient's body and then downstream returned to the patient's body. In other applications, the concentration process is carried out in a batch process, wherein an amount of the body fluid, tissues or cells is removed from the body as a unit, treated, and then returned to the patient's body as a unit.

SUMMARY

An aspect of the present disclosure relates to a fluid concentrator. The fluid concentrator includes a main housing and a cartridge removably engaged to the main housing. The main housing includes a first end portion having a first port and a second port, an oppositely disposed second end portion and a separation chamber that extends between the first and second end portions. The second end portion has an inlet port and defines a cartridge passage that extends through the second end portion. The separation chamber is in fluid communication with the inlet port. The cartridge defines a bore and includes a first axial end portion that is engaged with the first end portion and an oppositely disposed second axial end portion. The first axial end portion is engaged with the first end portion of the main housing when the cartridge is disposed in the main housing. A portion of the second axial end portion is disposed in the cartridge passage of the second end portion of the main housing when the cartridge is engaged with the main housing.

Another aspect of the present disclosure relates to a fluid concentrator. The fluid concentrator includes a main housing and a cartridge removably engaged to the main housing. The main housing includes a first end portion, an oppositely disposed second end portion and a separation chamber that extends between the first and second end portions. The first end portion includes a first surface and an oppositely disposed second surface. The second surface defines a first fluid port, a second fluid port and a cartridge opening. The second end portion has a first surface and an oppositely disposed second surface. The second surface defines an inlet port and a cartridge passage that extends through the first and second surfaces of the second end portion. The separation chamber is in fluid communication with the inlet port. The cartridge defines a bore and includes a first axial end portion and an oppositely disposed second axial end portion. The first axial end portion is disposed in the cartridge opening of the first end portion when the cartridge is engaged to the main housing. A portion of the second axial end portion is disposed in the cartridge passage of the second end portion of the main housing when the cartridge is engaged with the main housing. The cartridge is adapted to receive a material in a bore of the cartridge and to selectively receive fluid from the separation chamber.

The fluid concentrator has applications in medical treatments. In such embodiments, a body fluid or tissue is extracted from a patient. The extracted substance is separated into different fractions in the separation chamber and a portion of a selected fraction is transferred to the cartridge via the ports. The selected fraction is passed through a material in the cartridge, such as a filter or separation medium, to form a concentrated product that can be used in medical treatments or surgical procedures. Dependent upon which fraction is concentrated from the body fluid, the resultant concentrated product can be used to treat a variety of medical conditions.

The fluid concentrator also has applications in tissue regeneration, tissue culture, and cell culture. In such embodiments, the cartridge can be configured as a growth chamber for the engineering and culturing of tissue and cells. Growth material, scaffold material, graft material and the like can be inserted into the cartridge and concentrated body fluids, tissues, and/or cells can be transferred from the separation chamber via the ports to the growth material, scaffold material, or graft material in the cartridge.

A variety of additional aspects will be set forth in the description that follows. These aspects can relate to individual features and to combinations of features. It is to be understood that both the foregoing general description and the following detailed description are exemplary and explanatory only and are not restrictive of the broad concepts upon which the embodiments disclosed herein are based.

DRAWINGS

FIG. 6 is a top view of the fluid concentrator of FIG. 1.

DETAILED DESCRIPTION

Figure 1:
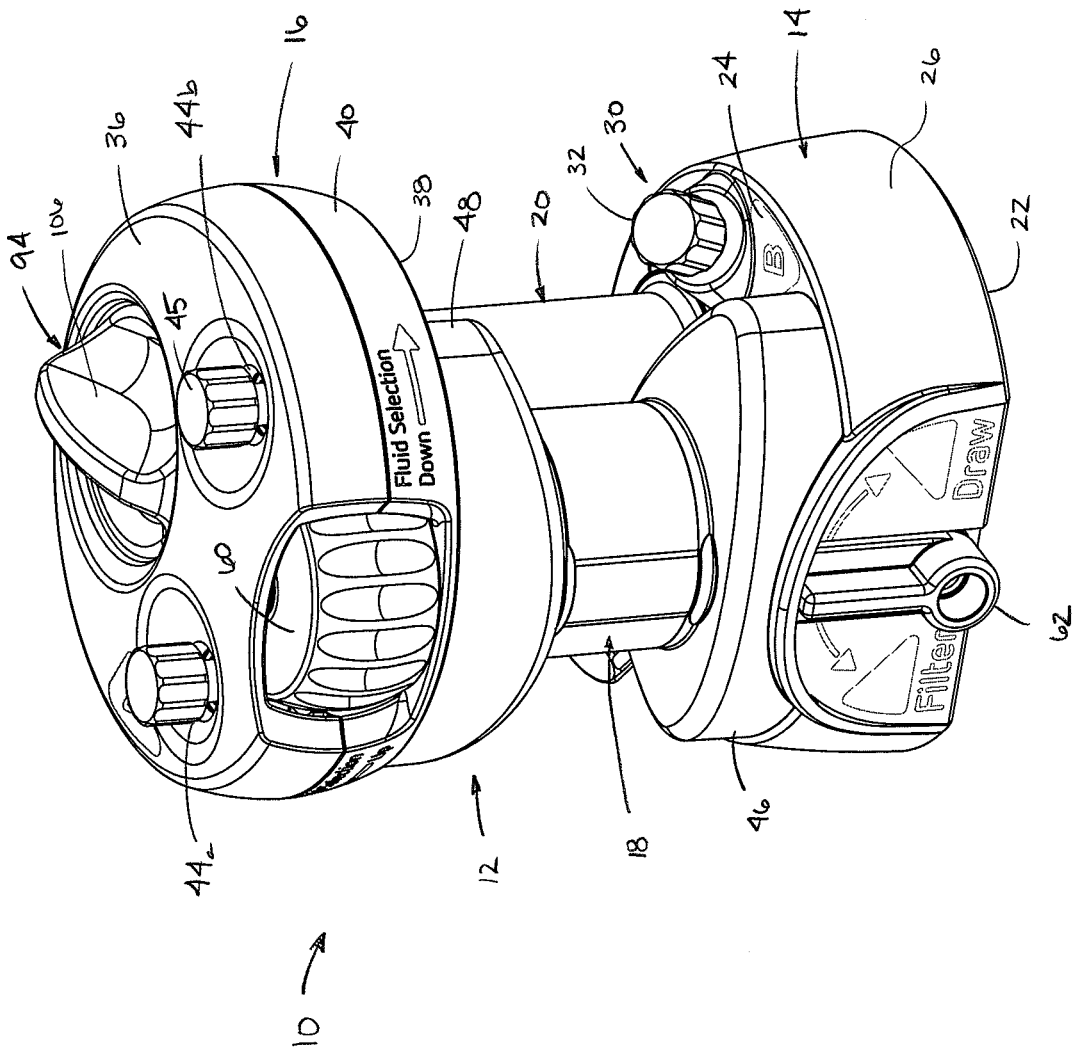
FIG. 1 is an isometric view of a fluid concentrator having exemplary features of aspects in accordance with the principles of the present disclosure.
Figure 2:
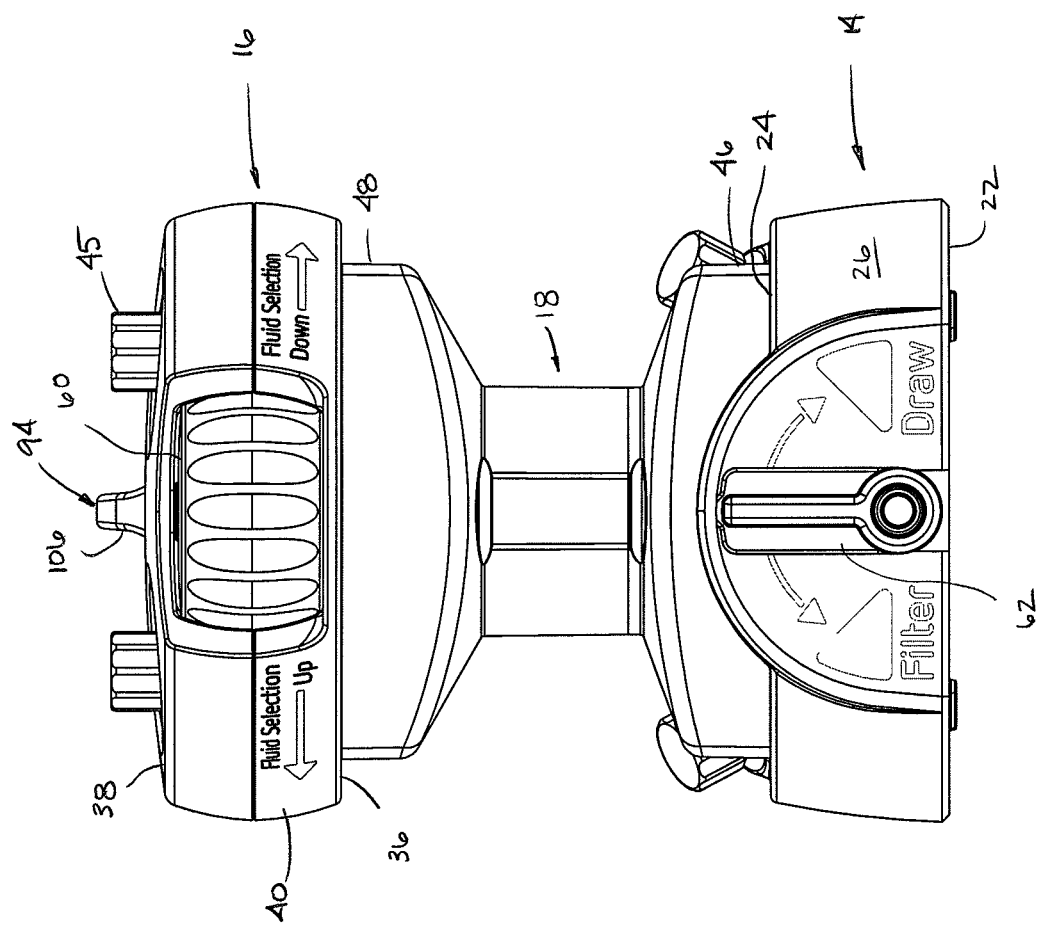
FIG. 2 is a front view of the fluid concentrator of FIG. 1.
Figure 3:
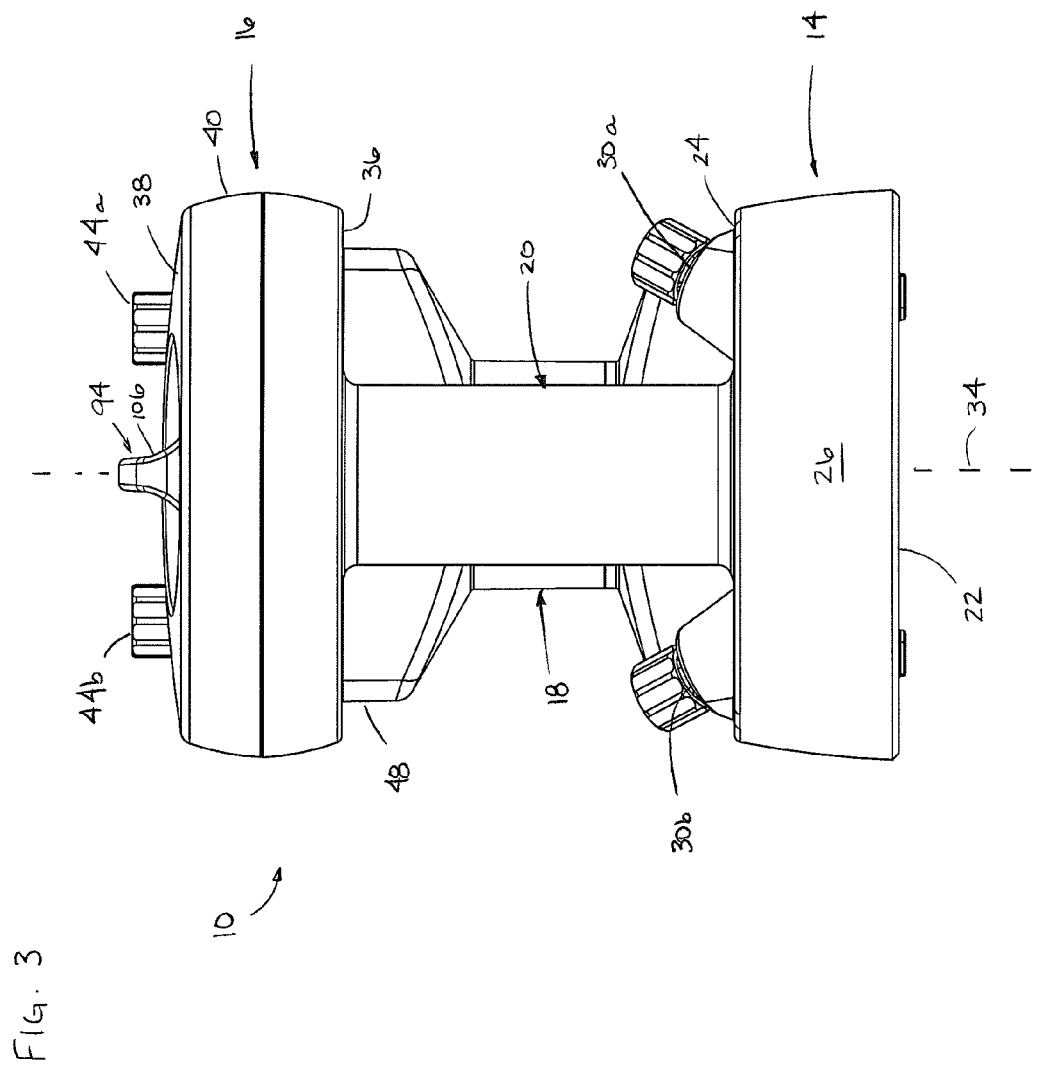
FIG. 3 is a back view of the fluid concentrator of FIG. 1.
Figure 4:
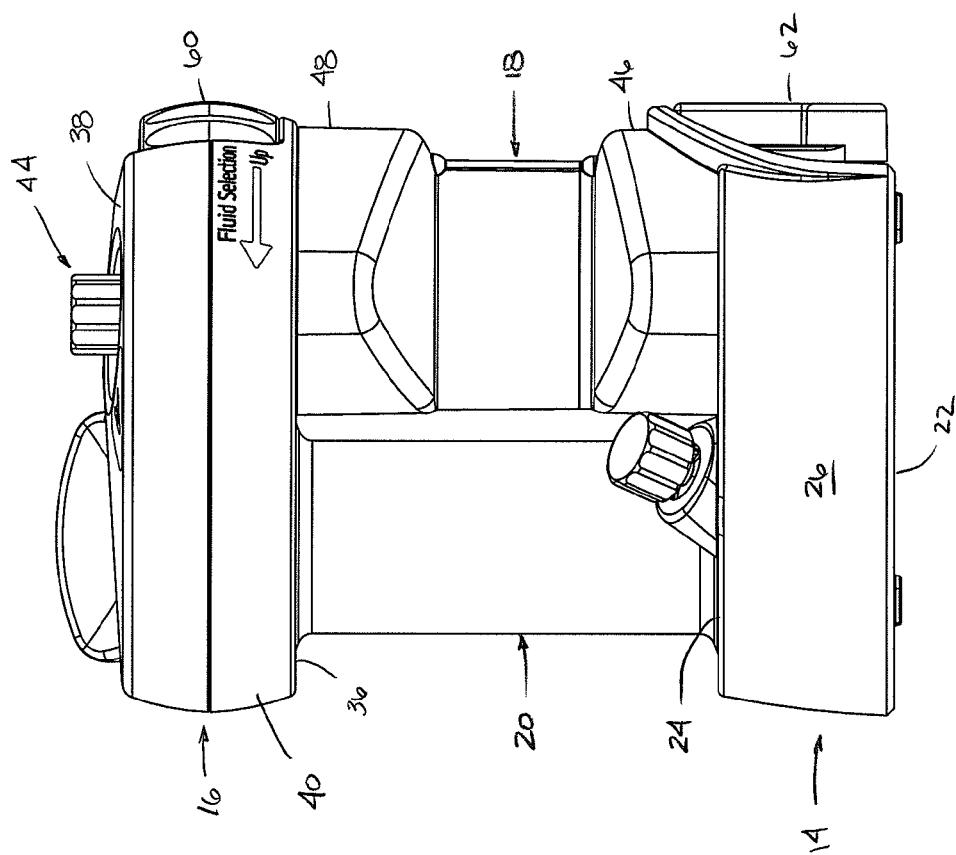
FIG. 4 is a right side view of the fluid concentrator of FIG. 1.

Reference will now be made in detail to the exemplary aspects of the present disclosure that are illustrated in the accompanying drawings. Wherever possible, the same reference numbers will be used throughout the drawings to refer to the same or like structure.

The term "body fluid" refers to a biological fluid collected from a subject. The subject can be a mammal, including but not limited to human, bovine, pig, sheep, horse, or goat. The body fluids can be autologous. Body fluids include, but are not limited to, blood, plasma, serum, urine, saliva, mucus, cerebrospinal fluid, lymphatic fluid, seminal fluid, amniotic fluid, vitreous fluid, as well as fluid collected from cell culture of patient cells, and the like. Body fluids can also include tissue and cells such as, for example, bone, bone marrow, muscle tissue, brain, heart, liver, lung, stomach, small intestine, large intestine, colon, uterus ovary, testis, cartilage, soft tissue, skin, subcutaneous tissue, breast tissue, tissue obtained from other species, patient tissue from surgery, and the like. The body fluids of the present disclosure also include, for example, bone marrow, fluids obtained from surgery, fluid filtrates, tissue filtrates or fragments, bone chips or fragments obtained during surgery, and the like.

Referring now to FIGS. 1-7, a fluid concentrator 10 is shown. The fluid concentrator 10 includes a main housing 12 having a first end portion 14, an oppositely disposed second end portion 16 and a separation chamber 18 that extends between the first and second end portions 14, 16. The fluid concentrator 10 further includes a cartridge 20 that is removably engaged to the main housing 12.

The cartridge 20, which will be described in greater detail subsequently, is configured to be inserted and removed from the main housing 12 while the main housing 12 is intact. This capability is potentially advantageous, for example, as it allows for different sterilization processes to be employed for the main housing 12 and the cartridge 20. In addition, it allows for the cartridge to be transported independently from the main housing 12 so that the contents of the cartridge can be subsequently independently processed (e.g., incubated, etc.).

While the cartridge 20 is shown as being empty in the depicted embodiments, the cartridge 20 is adapted to receive a material (e.g., objects, scaffolds (i.e., artificial structure capable of supporting tissue formation), graft materials, filters, cells, etc.). The cartridge 20 is in selective fluid communication with the separation chamber 18 so that fluid from the separation chamber 18 can be infused into the cartridge 20.

Figure 8:
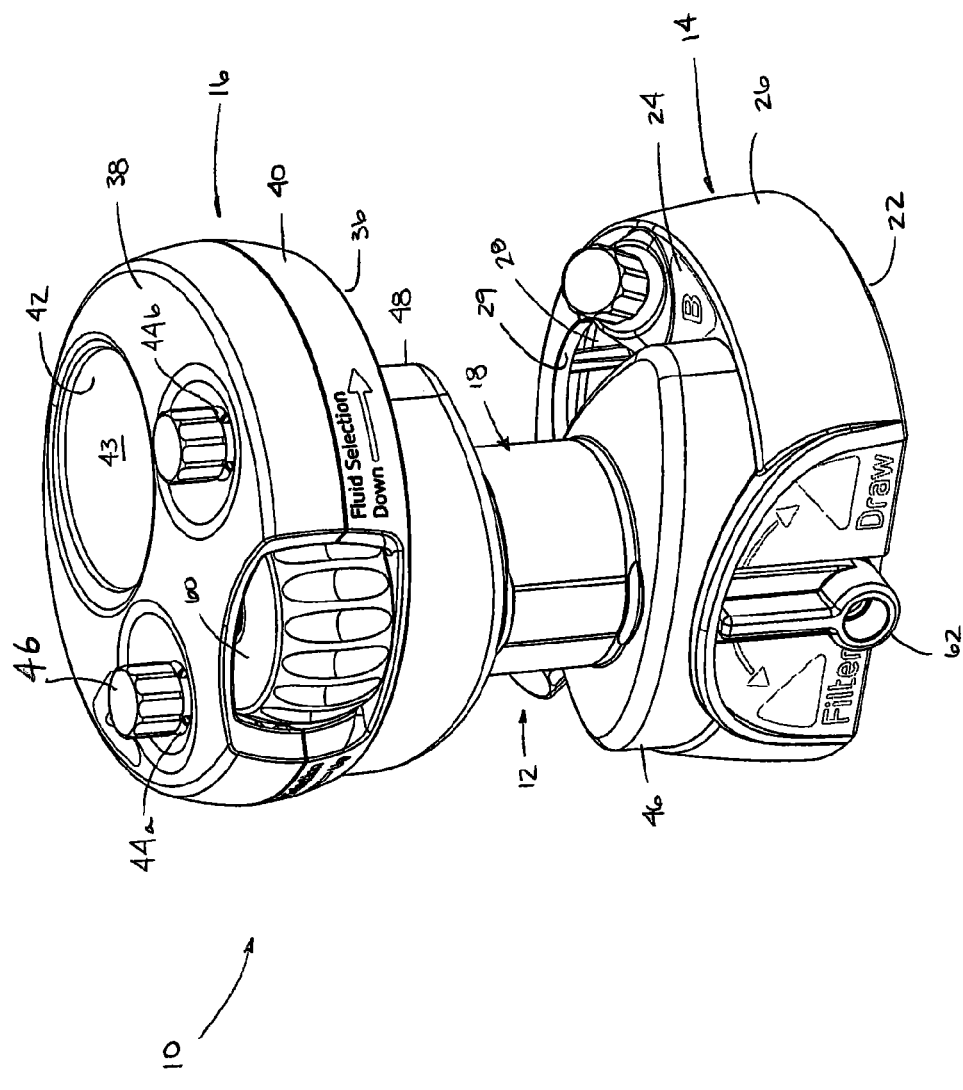
FIG. 8 is an isometric view of the fluid concentrator with a cartridge removed.
Figure 9:
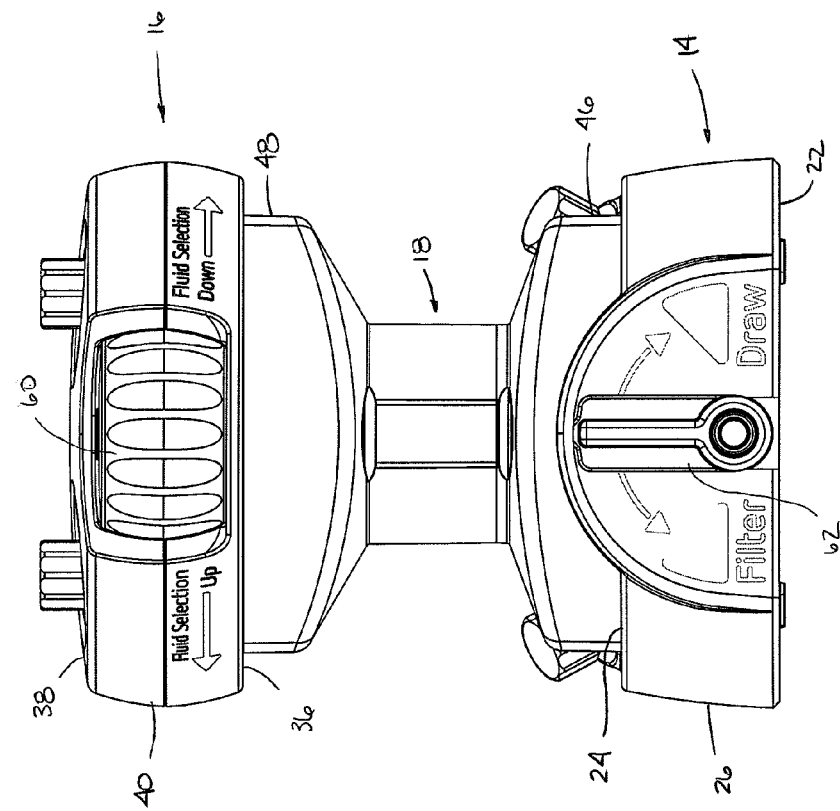
Figure 10:
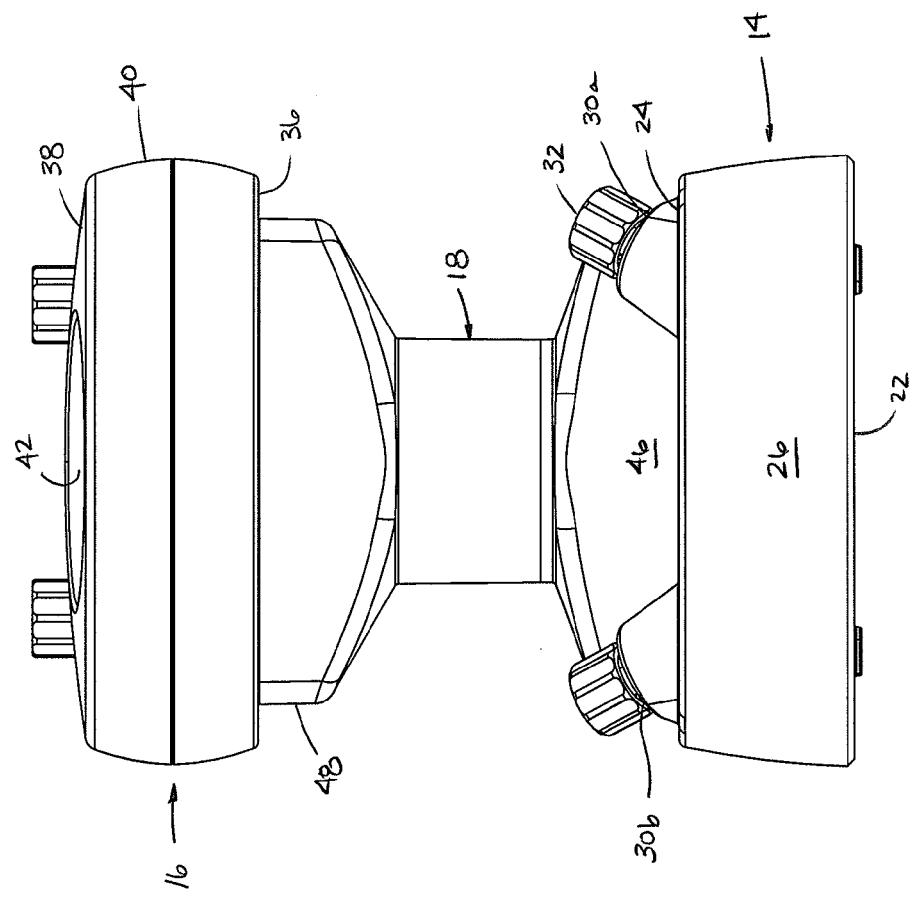
FIG. 10 is a back view of the fluid concentrator of FIG. 8.
Figure 11:
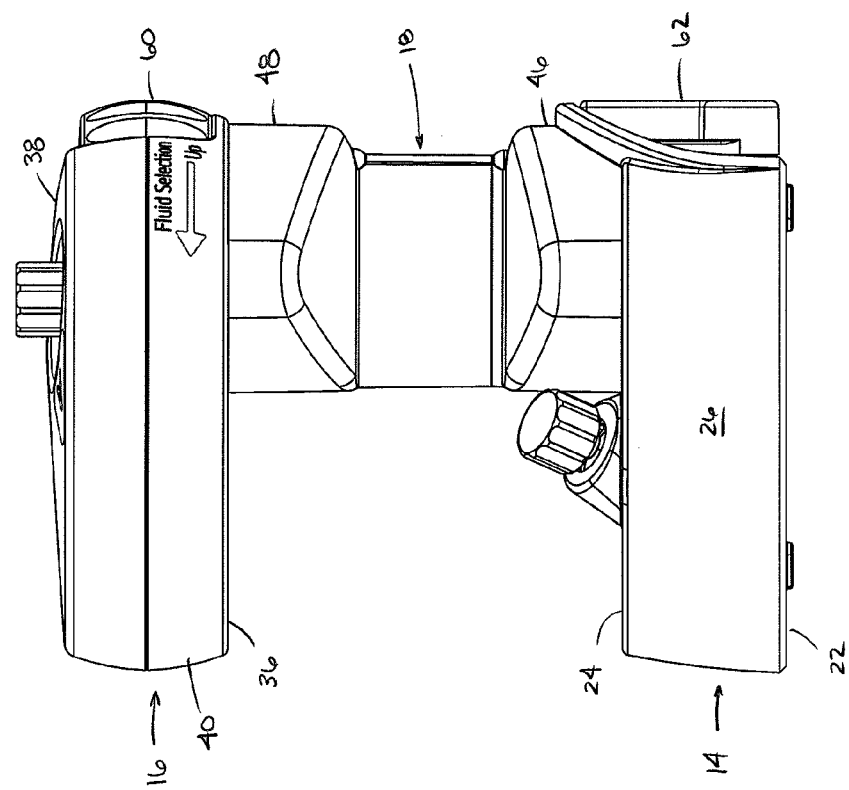
FIG. 11 is a right side view of the fluid concentrator of FIG. 8.
Figure 12:
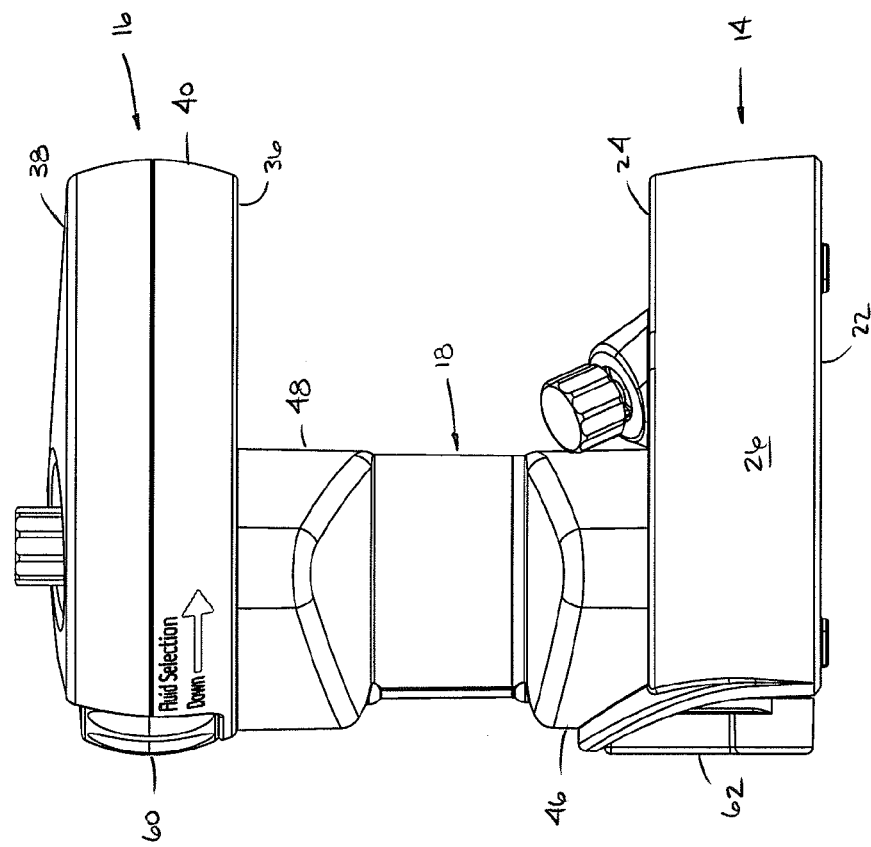
FIG. 12 is a left side view of the fluid concentrator of FIG. 8.
Figure 13:
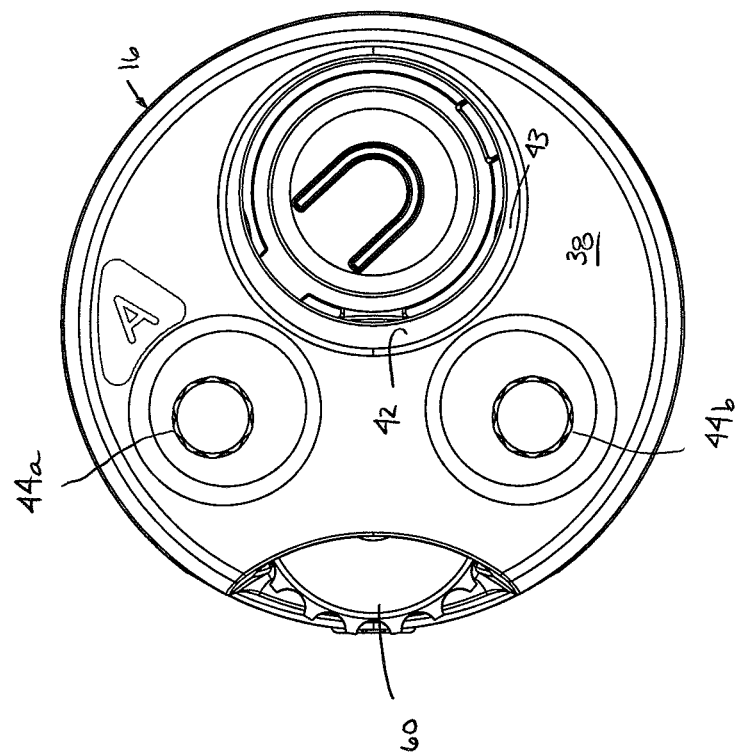
FIG. 13 is a top view of the fluid concentrator of FIG. 8.

In the orientation depicted in FIGS. 1-7, the first end portion 14 of the fluid concentrator 10 is a base portion. The first end portion 14 includes a first surface 22, an oppositely disposed second surface 24 and a sidewall 26 that extends between the first and second surfaces 22, 24. In the depicted embodiment, the first surface 22 is generally parallel to the second surface 24. The first and second surfaces 22, 24 and the sidewall 26 of the first end portion 14 cooperatively define an interior cavity 28 (shown in FIG. 8).

The second surface 24 defines a cartridge opening 29 that extends through the second surface 24. In the depicted embodiment, the cartridge opening 29 is generally circular in shape. The cartridge opening 29 provides access to the interior cavity 28 of the first end portion 14.

In one embodiment, the first end portion 14 is generally cylindrical in shape. In another embodiment, the first end portion 14 is generally frusto-conical in shape. In the depicted embodiment, the sidewall 26 tapers toward the second surface 24.

The first end portion 14 includes a base port 30. In the depicted embodiment, the first end portion 14 includes a first fluid port 30a and a second fluid port 30b. In the depicted embodiment, each of the first and second fluid ports 30a, 30b extends outwardly from the second surface 24 of the first end portion 14. The first and second fluid ports 30a, 30b extend outwardly in a direction that is oblique relative to the second surface 24. In the depicted embodiment, the first and second fluid ports 30a, 30b are angled toward the sidewall 26.

Each of the first and second fluid ports 30a, 30b includes an interior port interface and an exterior port interface. The interior port interface is disposed in the interior cavity 28 of the first end portion 14. The exterior port interface is accessible from an exterior of the fluid concentrator 10.

The interior port interfaces of the first and second fluid ports 30a, 30b are in fluid communication with at least one of the separation chamber 18 and the cartridge 20 through fluid conduits (e.g., tubing, flexible tubing, piping, etc.) disposed in the interior cavity 28. In one embodiment, the first fluid port 30a is in selective fluid communication with the separation chamber 18 and the cartridge 20. The second fluid port 30b is in fluid communication with the cartridge 20.

Each of the first and second fluid ports 30a, 30b are selectively capped by a plug 32. The plug 32 is engaged with the exterior port interface. In one embodiment, the plug 32 is threadedly engaged with the exterior port interface of each of first and second fluid ports 30a, 30b, respectively.

In the orientation depicted in FIGS. 1-14, the second end portion 16 of the fluid concentrator 10 is a top portion. The second end portion 16 is generally aligned with the first end portion 14. In the depicted embodiment, the second end portion 16 is generally aligned along a central longitudinal axis 34 of the fluid concentrator 10 that extends through the first and second end portions 14, 16. The second end portion 16 includes a first surface 36, an oppositely disposed second surface 38 and a sidewall 40 that extends between the first and second surfaces 36, 38.

In one embodiment, the second end portion 16 is generally disc-shaped (or puck-shaped). In the depicted embodiment, the sidewall 40 is generally arcuate in shape so that the outer diameter of a central region 41 of the sidewall 40 is greater than an outer diameter of the sidewall 40 at the first surface 36 and an outer diameter of the sidewall 40 at the second surface 38.

The second end portion 16 defines a cartridge passage 42 that extends through the first and second surfaces 36, 38. In the depicted embodiment, the cartridge passage 42 includes an inner wall 43 that circumferentially surrounds the cartridge passage 42. In another embodiment, the cartridge passage 42 is generally U-shaped and includes an opening in the sidewall 40 of the second end portion 16.

The cartridge passage 42 is adapted to receive the cartridge 20. The cartridge passage 42 is configured so that the cartridge 20 can be inserted and removed from the fluid concentrator 10 while the main housing 12 is intact.

The second end portion 16 includes an inlet port 44. In the depicted embodiment, the second end portion 16 includes a first inlet port 44a and a second inlet port 44b. The first and second inlet ports 44a, 44b are configured to be in fluid communication with the separation chamber 18.

Each of the first and second inlet ports 44a, 44b includes an interior port interface and an exterior port interface. The interior port interface is in fluid communication with the separation chamber 18. The exterior port interface is accessible from an exterior of the fluid concentrator 10.

In the depicted embodiment, each of the first and second inlet ports 44a, 44b extends outwardly from the second surface 38 of the second end portion 16. In the depicted embodiment, the first and second inlet ports 44a, 44b extend outwardly in a direction that is generally parallel to the central longitudinal axis 34 of the fluid concentrator 10.

Each of the first and second inlet ports 44a, 44b are selectively capped by a plug 45. The plug 45 is engaged with the exterior port interface. In one embodiment, the plug 45 is threadedly engaged with the exterior port interface of each of first and second inlet ports 44a, 44b, respectively.

The separation chamber 18 extends between the first and second end portions 14, 16. The separation chamber 18 is adapted to contain a concentrated fluid. The term "concentrated" refers to a fluid which has been separated by gravity, centrifugation, and/or filtration into various fractions. The term fraction refers to the various components into which a biological fluid can be separated by centrifugation, gravitational weight separation and/or filtration. Each fraction is richer in a particular fluid component (i.e. concentrated) relative to the other fraction and the original fluid. The concentration process also removes nonessential components such that the concentrated fraction contains only necessary or desired components.

The separation chamber 18 includes a first end 46 and an oppositely disposed second end 48. The first end 46 is engaged to the second surface 24 of the first end portion 14 while the second end 48 is engaged to the first surface 36 of the second end portion 16. The separation chamber 18 defines an interior cavity 50. The interior cavity 50 is adapted to receive fluid. In the depicted embodiment, the first and second inlet ports 44a, 44b are in fluid communication with the interior cavity 50 of the separation chamber 18.

Figure 5:
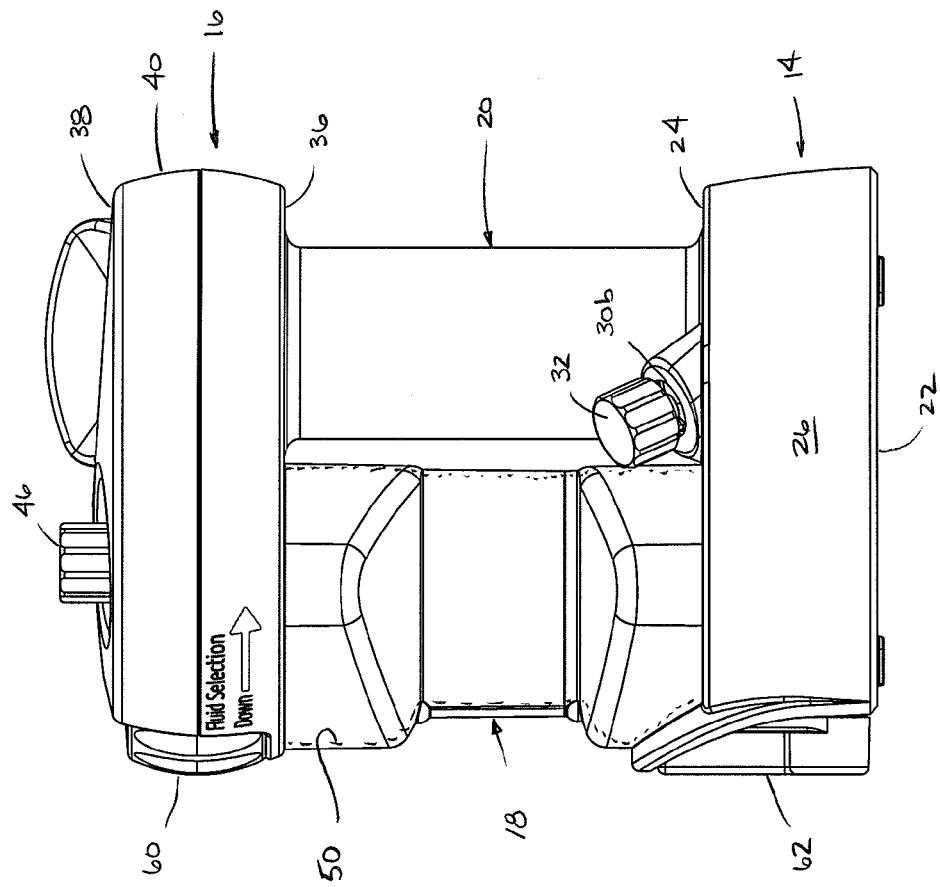
FIG. 5 is a left side view of the fluid concentrator of FIG. 1.
Figure 9:
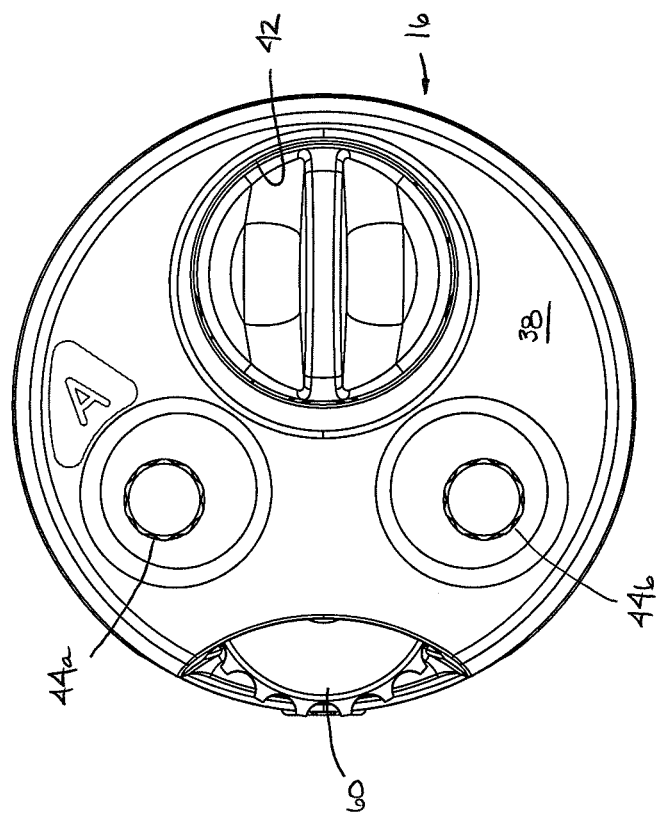
FIG. 9 is a front view of the fluid concentrator of FIG. 8.
Figure 7:
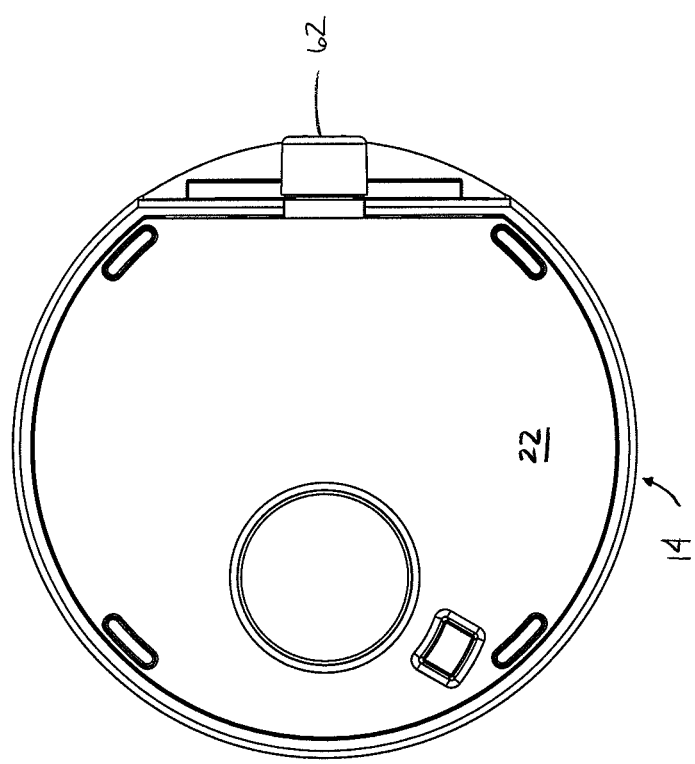
FIG. 7 is a bottom view of the fluid concentrator of FIG. 1.
Figure 14:
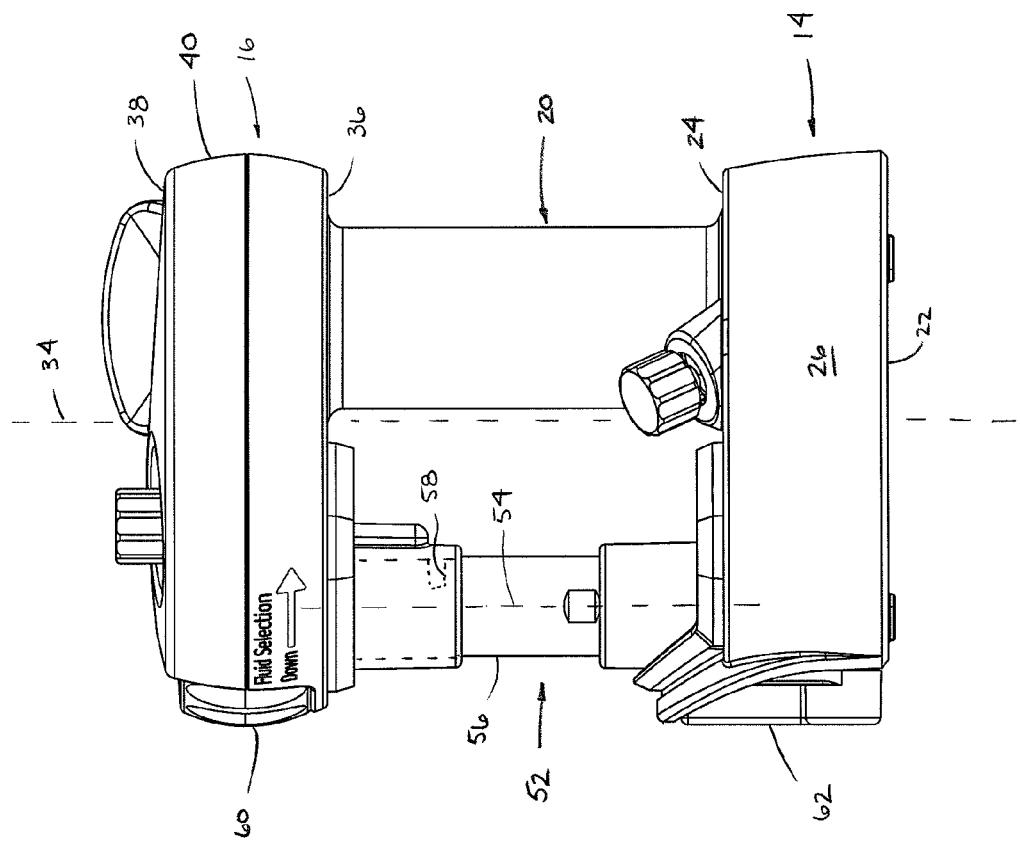
FIG. 14 is a left side view of the fluid concentrator of FIG. 1 with a separation chamber removed to show a valve assembly suitable for use with the fluid concentrator.

Referring now to FIGS. 1, 5 and 14, the fluid concentrator 10 includes a valve assembly 52 that is in fluid communication with the separation chamber 18. The valve assembly 52 defines a longitudinal axis 54 that is generally parallel to the central longitudinal axis 34 of the fluid concentrator 10. The valve assembly 52 includes a valve stem 56 that defines a fluid opening 58. The valve stem 56 is axially positionable along the longitudinal axis 54 in the interior cavity 50 of the separation chamber 18. After centrifugation, the valve stem 56 can be axially positioned so that a height of the fluid opening 58 corresponds to a desired fluid layer. The fluid opening 58 thus serves as an outlet port from which a fraction of fluid in the separation chamber 18 can be removed.

The valve assembly 52 further includes a valve adjustment knob 60. The valve adjustment knob 60 is adapted to rotate about the longitudinal axis 54. In one embodiment, the valve adjustment knob 60 is in threaded engagement with the valve stem 56. As the valve adjustment knob 60 is rotated in a first direction about the longitudinal axis 54, the fluid opening 58 moves toward the first end portion 14. As the valve adjustment knob 60 is rotated in an opposite second direction about the longitudinal axis 54, the fluid opening 58 moves toward the second end portion 16.

In the depicted embodiment, the valve adjustment knob 60 is disposed in the second end portion 16 of the fluid concentrator 10. In the depicted embodiment, a portion of the sidewall 40, which is adjacent to the separation chamber 18, of the second end portion 16 is recessed so that a portion of the valve adjustment knob 60 can be accessed.

The valve assembly 52 further includes a control handle 62. In the depicted embodiment, the control handle 62 is moveable between a first position and a second position. In the first position, the fluid opening 58 is in fluid communication with the first fluid port 30a in the first end portion 14 of the fluid concentrator 10. In the second position, the first fluid port 30a is in fluid communication with the cartridge 20.

Figure 15:
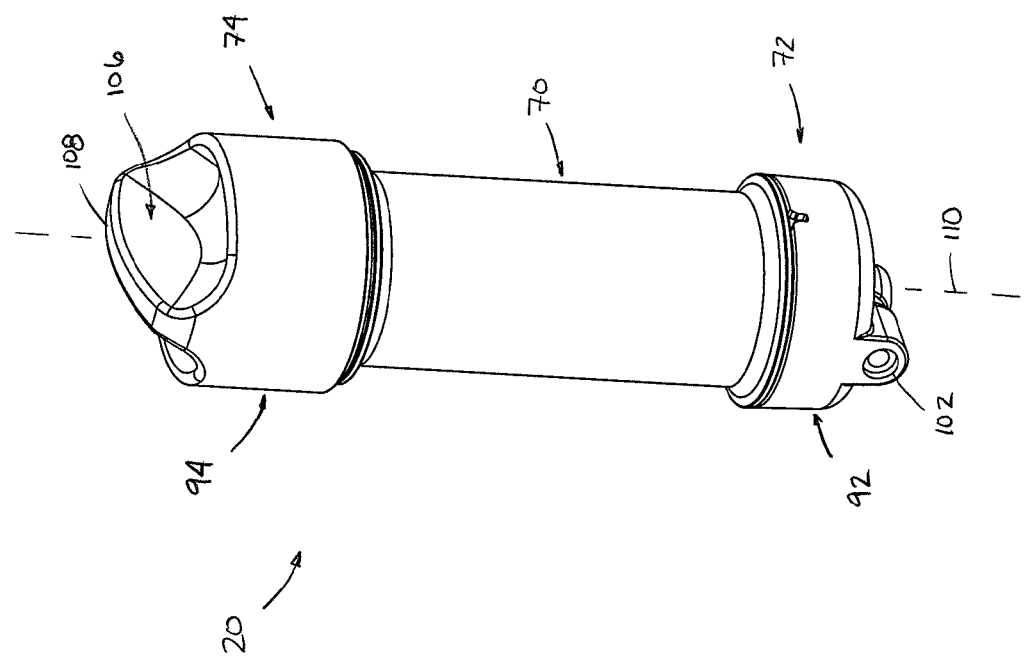
FIG. 15 is an isometric view of a cartridge that is suitable for use with the fluid concentrator of FIG. 1.
Figure 16:
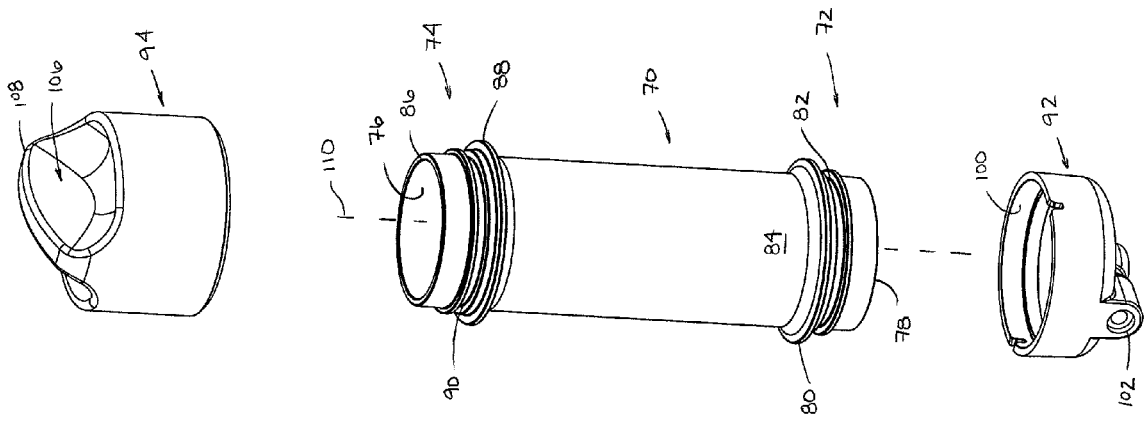
FIG. 16 is an exploded isometric view of the cartridge of FIG. 15.

Referring now to FIGS. 1, 15 and 16, the cartridge 20 is shown. The cartridge 20 is configured to be received by the first and second end portions 14, 16 of the fluid concentrator 10 and to be in fluid communication with the separation chamber 18.

In the depicted embodiment, the cartridge 20 includes a body 70 having a first axial end portion 72 and an oppositely disposed second axial end portion 74. The body 70 defines a bore 76 that extends through the first and second axial end portions 72, 74.

The first axial end portion 72 includes a first axial end 78 and a first shoulder 80. The first shoulder 80 extends radially outwardly from the body 70. The first axial end portion 72 defines a first groove 82 that is disposed between the first axial end 78 and the first shoulder 80. The first groove 82 is a circumferential groove defined in an outer surface 84 of the body 70.

The second axial end portion 74 includes a second axial end 86 and a second shoulder 88. The second shoulder 88 extends radially outwardly from the body 70. The second axial end portion 74 defines a second groove 90 that is disposed between the second axial end 86 and the second shoulder 88. The second groove 90 is a circumferential groove defined in the outer surface 84 of the body 70.

The fluid concentrator has numerous applications, including medical treatments and therapies, tissue regeneration, tissue culture, and cell culture. In an embodiment, a body fluid or tissue is extracted from a patient. The extracted fluid or tissue is separated into different fractions in separation chamber 18 and a portion of a selected fraction is transferred to cartridge 20 via the ports. The selected fraction is passed through a material in cartridge 20, such as a filter or separation medium, to form a concentrated product that can be used in medical treatments or surgical procedures. Dependent upon which fraction is concentrated from the body fluid, the resultant concentrated product can be used to treat a variety of conditions. Various different concentrated body fluids can be prepared as described above including, without limitation, blood fractions, platelet rich plasma (PRP), platelet poor plasma (PPP), stem cells (cord blood-derived and bone marrow-derived), concentrated seminal flood, concentrated spinal fluid, and the like.

Dependent upon the body fluid or tissue and which fraction is concentrated from the body fluid or tissue, the resultant product can be used to treat a variety of medical conditions including, but not limited to a wound, soft tissue injury, or surgical site. The wound can be a surgical incision, abrasion, ulcer, burn, or other break in the skin. The resultant product can also be administered to treat an orthopedic disorder or during or after a surgical procedure to correct the orthopedic disorder to promote healing. Examples of orthopedic disorders include without limitation spinal fusion, spinal defect, bone trauma, cartilage damage, bone cyst, bone tumor, bone fracture, filling of osseous defect, joint augmentation, sinus augmentation, ridge preservation, joint revision, posterolateral fusion, and the like.

In other embodiments, cartridge 20 can be configured as a growth chamber for the engineering and culturing of tissue and cells. Growth material, scaffold material, and the like can be inserted into the cartridge and concentrated body fluids, tissues, and/or cells can be transferred from separation chamber 18 via the ports to the growth material or scaffold material in cartridge 20. In an embodiment, tissue is disrupted and then separated into fractions in separation chamber 18. A desired cellular fraction is transferred from separation chamber 18 via the transfer ports to cartridge 20 configured with a growth material or scaffold. The cellular fraction can be cultured within the fluid concentrator or cartridge 20 can be removed and cultured separately from the fluid concentrator.

In one embodiment, the bore 76 of the body 70 is adapted to receive a material. The material can a separation medium, a filtration medium, a growth matrix or surface, scaffold, graft material or other material selected by a user. Separation and/or filtration media include affinity columns, packed bed matrices and beads. Nanofiber networks can be used as filtration media or as a growth matrix or growth surface. Nanofiber networks and methods of making nanofiber networks are known and commercially available from Surmodics (Minneapolis, Minn.). See, for example, WO 2006/094076, U.S. 2005/0095695 and U.S. 2007/0082393. Objects such as a rod, screw, wire, mesh, or cage can also be used as a growth surface or scaffold. In embodiments, the material inserted into bore 76 of the body 70 is selected such that cartridge 20 can be utilized as a reaction chamber, holding chamber, or culture chamber to collect and retain separated fraction and/or filtered fluids or cells.

In one embodiment, the material can comprise an affinity membrane, support or column. Affinity columns used in chromatographic separation or purification of proteins and other biological macromolecules make use of specific binding interactions between molecules. In an aspect, a particular ligand is chemically immobilized or "coupled" to a solid support. Ligands that bind to general classes of proteins (such as, for example, receptors or antibodies) or commonly used fusion protein tags (such as, 6xHis) are commercially available in pre-immobilized forms ready to use for affinity purification. Alternatively, more specialized ligands such as specific antibodies, antigens or receptors of interest can be immobilized using one of several commercially available activated affinity supports. For example, a peptide antigen can be immobilized to a support and used to purify antibodies that recognize the peptide. Similarly, a receptor that binds a growth factor, differentiation factor, chemotactic factor, or adhesion molecule can be immobilized to a support and used to purify said factors or molecules in the concentrated fraction of body fluids. Antibodies and receptors that bind growth factors, differentiation factors, chemotactic factors, or and/or adhesion molecules methods of making such antibodies and receptors, and methods of immobilizing the antibodies and receptors on a support are known.

One or more ligands can be attached to the material. The ligands can be selected to bind one or more particular growth factors, differentiation factors, chemotactic factors, and/or adhesion molecules. The ability to attach one or more selected ligands to the material provides for the creation of a custom body fluid, scaffold, or growth matrix, wherein the particular bioactive molecules comprising the concentrated body fluid, scaffold, or growth matrix are defined, for example, by the particular ligands, concentration of ligands, and/or ratio of one ligand to another selected by the user.

Ligands can be immobilized or "coupled" directly to a solid support material, growth surface, scaffold, and the like by formation of covalent chemical bonds between particular functional groups on the ligand and reactive groups on the support material, growth surface, or scaffold. Examples of functional groups and reactive groups include, without limitation, primary amines, sulfhydryls, carboxylic acids, aldehydes, and the like. However, other coupling approaches are also possible. For example, a GST-tagged fusion protein can be first bound to an immobilized glutathione support by affinity interaction with the GST tag and then chemically cross-linked to the support. The immobilized GST-tagged fusion protein can then be used to affinity purify its binding partner(s).

In another embodiment, the material can comprise affinity or chromatography beads or particles. The beads or particles can be, for example, glass, alginate, polymeric, or magnetic beads or particles. The beads or particles function in the same way as affinity matrices or columns, but are significantly reduced in size, and are therefore particularly useful for microscale biological manipulations. In embodiments, an affinity column or affinity bead or particle is used as the material of the fluid concentrator 10 such that when a separated fluid or fluid fraction is passed over the beads or particles, those molecules or fluid components that have specific binding affinity to the ligand are retained on the beads, and can be retrieved or isolated by subsequent elution.

In another embodiment, the material can comprise a packed bed matrix or column. A packed bed is a bed of granular material which retains the solid particles as it passes, allowing fluids and liquids to be filtered free of solid contaminants or components. In an aspect, the granular material for the packed bed can be sand, although celite or diatomaceous earth packed in a microscale container or loaded on top of a sintered-glass funnel can also serve as the packed bed. Incompressible diatomaceous earth (i.e. primarily silica), wood cellulose or other inert porous solids can also be used as the granular material of the packed bed filter.

In another embodiment, a packed bed matrix or column is used as the material of the fluid concentrator 10 such that when the separated fluid or fluid fraction is passed over the column, solid components or fluid components with a size greater than the pore size of the packed bed material are retained on the packed bed, while other fluid components pass through.

In another embodiment, the material can comprise a network of one or more nanofibers, a nanofibrillar structure, glass, silicon, or plastic comprising an etched or micropatterned surface, glass, silicon, or plastic surface comprising macropores or nanopores, or a polymer scaffold. Nanofiber networks of this type are described in WO 2006/094076, U.S. 20050059695, and U.S. 20070082393 for example. The nanofiber network can be deposited on a surface of a substrate, and the combination of the nanofiber on the substrate can be a growth matrix or substrate, or as a filtration membrane. In some embodiments, the substrate can be glass, polymeric, metallic, ceramic, cellulosic, or proteinaceous. Examples of a substrate include but are not limited to a rod, screw, wire, mesh, or cage. The nanofibrillar structure or nanofiber networks can be utilized singly or layered to form a multi-layered assembly of nanofibrillar structures or nanofiber networks for cell or tissue culture.

In some embodiments, the nanofibrillar structure is used as a filter element or membrane of the concentrator device, such that when a separated fluid, fluid fraction, or cellular fraction is passed over the filter element, solid components or fluid components with a size greater than the pore size of the nanofibrillar material are retained on the material, while other fluid components pass through. In other embodiments, the nanofibrillar structure can be a growth matrix or scaffold, such that when the separated fluid, fluid fraction, or cellular fraction is passed over the matrix or scaffold, growth factors in the fluid, fluid fraction, or cellular fraction are retained on the matrix or scaffold and can be used to support subsequent cell or tissue growth.

The cartridge 20 further includes a first end cap 92 and a second end cap 94. The first end cap 92 is engaged to the first axial end portion 72 of the body 70 while the second end cap 94 is engaged to the second axial end portion 74 of the body 70. In the depicted embodiment, the first and second end caps 92, 94 are sealingly engaged with the first and second axial end portions 72, 74, respectively. In one embodiment, the first and second end caps 92, 94 are in threaded engagement with the first and second axial end portions 72, 74, respectively. In another embodiment, the first and second end caps 92, 94 are in tight fitting engagement with the first and second axial end portion 72, 74. In another embodiment, the first and second end caps 92, 94 are sonically welded to the first and second axial end portions 72, 74, respectively.

In the depicted embodiment, a first seal provides the sealing engagement between the first end cap 92 and the first axial end portion 72 while a second seal provides the sealing engagement between the second end cap 94 and the second axial end portion 74. In one embodiment, the first and second seals are o-rings. In another embodiment, the first and second seals are gaskets. The first seal is disposed in the first groove 82 defined by the first axial end portion 72. The second seal is disposed in the second groove 90 defined by the second axial end portion 74.

The first end cap 92 defines a first cavity 100 that is adapted to receive the first axial end 78 of the body 70 of the cartridge 20. The first end cap 92 includes a first port 102 that is in fluid communication with the bore 76 of the body 70 when the first end cap 92 is disposed on the first axial end portion 72 of the cartridge 20. The first end cap 92 further includes a second port 103 (shown in FIGS. 18 and 19) that is in fluid communication with the bore 76 of the body 70 when the first end cap 92 is disposed on the first axial end portion 72 of the cartridge 20. The first port 102 is in selective fluid communication with the first fluid port 30a while the second port 103 is in fluid communication with the second fluid port 30b.

The second end cap 94 defines a second cavity that is adapted to receive the second axial end 86 of the body 70. The second end cap 94 includes a gripping portion 106. In the depicted embodiment, the gripping portion 106 includes a protrusion 108 that extends outwardly in a direction along a longitudinal axis 110 of the body 70. The protrusion 108 is adapted to be grasped by a hand of a user.

Figure 17:
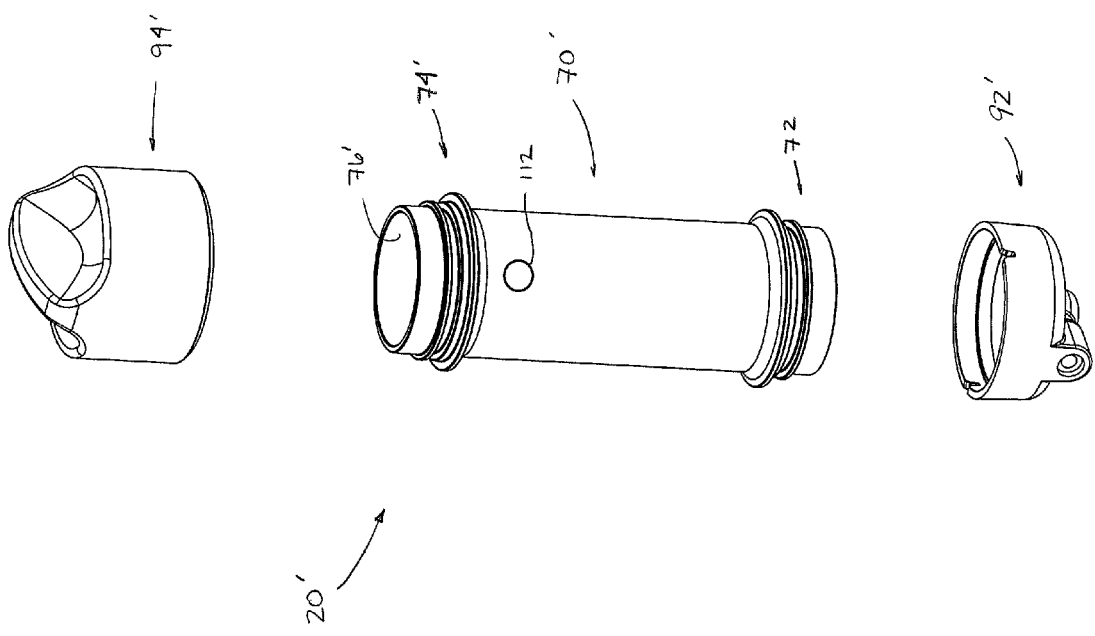
FIG. 17 is an exploded isometric view of an alternate embodiment of a cartridge suitable for use with the fluid concentrator of FIG. 1.

Referring now to FIG. 17, an alternate embodiment of a cartridge 20' is shown. The cartridge 20' is similar to the cartridge 20 that was previously described. It will be understood that the features disclosed with regard to the cartridge 20 could be used with the cartridge 20'.

The cartridge 20' includes a body 70' having a first axial end portion 72' and an oppositely disposed second axial end portion 74'. The body 70' defines a bore 76' that is adapted to receive the material. The bore 76' is further adapted to selectively receive fluid from the first fluid port 30a of the fluid concentrator 10.

The cartridge 20' further includes a first end cap 92' and a second end cap 94'. The first end cap 92' is engaged to the body 70' at the first axial end portion 72' while the second end cap 94' is engaged to the body 70' at the second axial end portion 74'.

The first end cap 92' of the cartridge 20' defines a first port 102' and a second port. The first port 102' is in selective fluid communication with the first fluid port 30a of the fluid concentrator 10. The second port is in fluid communication with the second fluid port 30b of the fluid concentrator 10.

The cartridge 20' further defines a third port 112. The third port 112 (shown schematically in FIG. 17) provides access to the bore 76' of the body 70' of the cartridge 20'. In the depicted embodiment, the third port 112 is disposed adjacent to the second axial end portion 74' of the cartridge 20'. In another embodiment, the third port 112 is disposed adjacent to the first axial end portion 72'. In another embodiment, the third port 112 is disposed between the first and second axial end portions 72', 74'. In another embodiment, the third port 112 is defined by the first end cap 92'. In another embodiment, the third port 112 is defined by the second end cap 94'.

The third port 112 provides a location at which additional materials can be added or injected into the bore. The additional materials can include cells, growth factors, food, drugs, chemicals, combinations thereof, etc.

Figure 18:
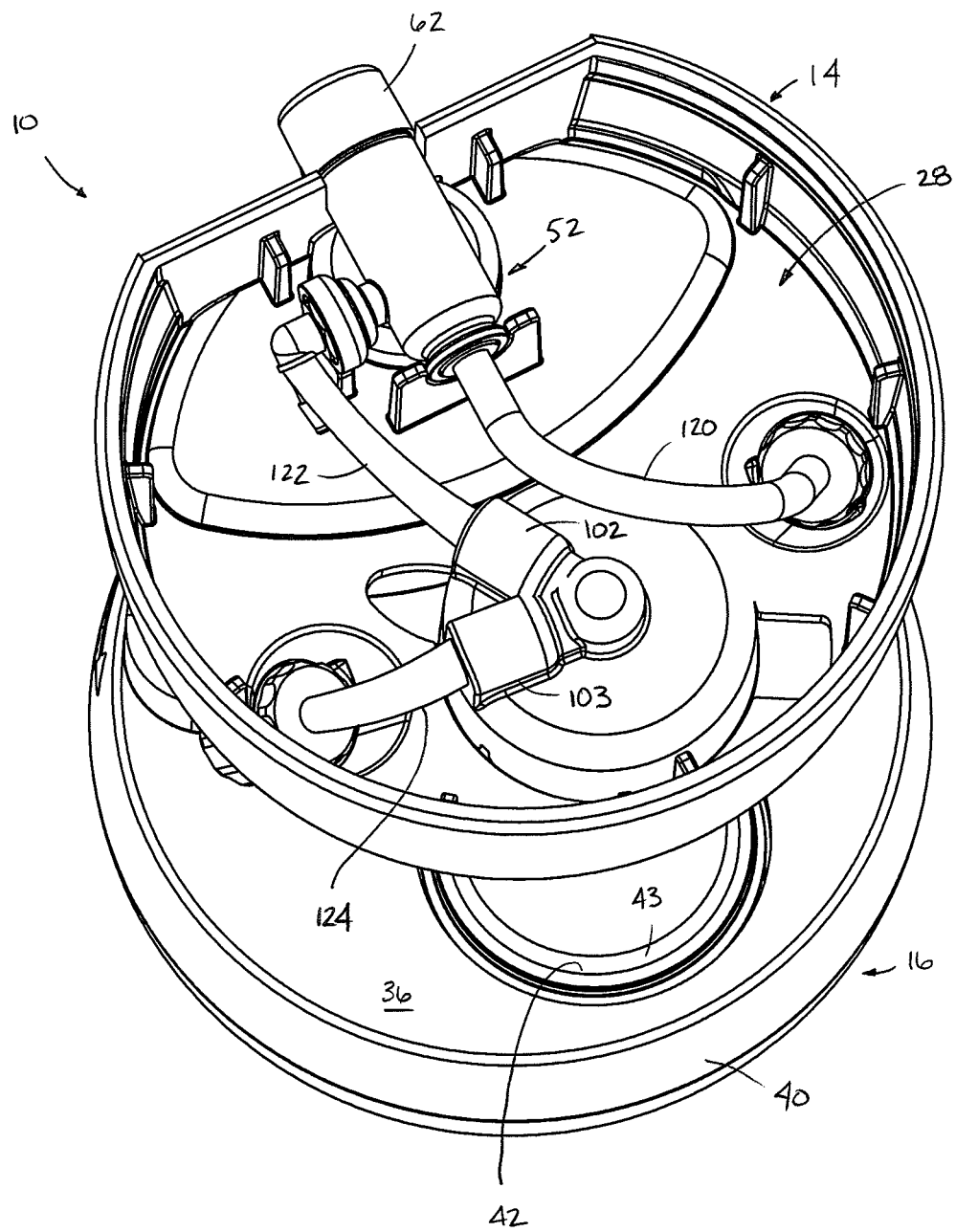
FIG. 18 is an isometric view of an interior region of a first end portion of the fluid concentrator of FIG. 1.
Figure 19:
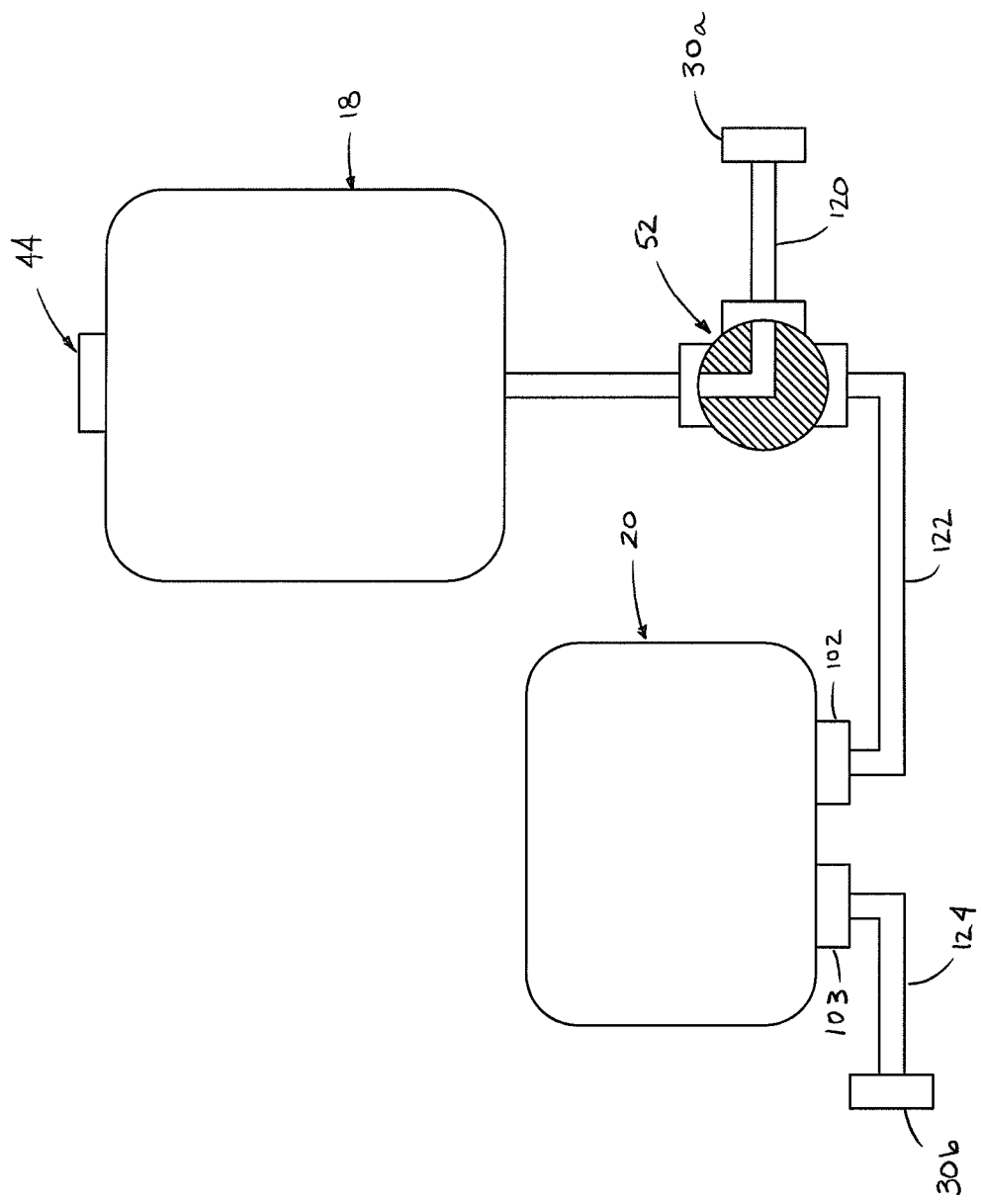
FIG. 19 is a schematic representation of a fluid path through the fluid concentrator of FIG. 1.

Referring now to FIGS. 18 and 19, the routing of fluid in the fluid concentrator 10 will be described. A first fluid conduit 120 provides a selective fluid passage between the first fluid port 30a in the first end portion 14 of the fluid concentrator 10 and the fluid opening 58 in the valve assembly 52. A second fluid conduit 122 provides a selective fluid passage between the valve assembly 52 and the port 102 of the cartridge 20. A third conduit 124 provides a fluid passage between the second fluid port 30b and the second port 103 of the cartridge 20.

In the depicted embodiment, the control handle 62 is actuated between the first and second positions. In the first position, fluid communication between the separation chamber 18 and the first fluid port 30a is established through the first fluid conduit 120. In the second position, fluid communication between the first fluid port 30a and the first port 102 of the cartridge 20 is established through the first and second fluid conduits 120, 122. Filtered fluid can be removed from the second fluid port 30b of the first end portion 14 of the fluid concentrator through the third conduit 124.

Referring now to FIGS. 1, 8-13 and 15-16, the assembly of the cartridge 20 into the fluid concentrator 10 will be described. With a filter disposed in the bore 76 of the body 70 of the cartridge 20 and the first and second end caps 92, 94 disposed on the first and second axial end portions 92, 94, the first end cap 92 and the first axial end portion 72 of the body 70 are inserted through the cartridge passage 42 of the second end portion 16 of the fluid concentrator 10 in a direction toward the first end portion 14. When the first end cap 92 is adjacent to the first end portion 14 of the fluid concentrator 10, tubing 100 (shown in FIG. 24) is connected to the cartridge 20 to establish fluid communication between the cartridge 20 and the first and second fluid ports 30a, 30b and the separation chamber 18. With the fluid communication between the cartridge 20 and the first and second fluid ports 30a, 30b and the separation chamber 18 established, the first end cap 92 of the cartridge 20 is inserted through the cartridge opening 29 of the second surface 24 of the first end portion 14. In the depicted embodiment, with the first end cap 92 engaged in the cartridge opening 29, a portion of the second end cap 94 is disposed in the cartridge passage 42 of the second end portion 16.

Fluid is inserted through the inlet port 44 of the second end portion 16. The fluid passes through the inlet port 44 into the separation chamber 18. The fluid concentrator 10 is put into a centrifuge to separate the layers of the fluid. With the fluid separated, the valve adjustment knob 60 is actuated to position the fluid opening 58 of the valve stem 56 of the valve assembly 52 at the desired height of the fluid layer of interest.

In some embodiments, the filter element or membrane in the cartridge 20 is not tolerant of centrifugation. In such instances, the cartridge 20 is disengaged from the main housing 12 prior to centrifugation and reengaged after centrifugation.

The control handle 62 is actuated to the first position, which provides fluid communication between the separation chamber 18 and the first fluid port 30a. Fluid from the fluid layer is then withdrawn from the separation chamber 18 through the fluid opening 58 and through the first fluid port 30a. In one embodiment, a syringe draws the fluid through the first fluid port 30a.

The control handle 62 is actuated to second position, in which fluid communication is established between the first fluid port 30a and the cartridge 20. The fluid is then pushed into the first fluid port 30a and the cartridge 20. In one embodiment, fluid is drawn out of the cartridge 20 through the second fluid port 30b.

The cartridge 20 can be removed from the fluid concentrator 10 by pulling on the gripping portion 106 of the second end cap 94 of cartridge 20 in an axial direction away from the first end portion 14 of the fluid concentrator 10. In one embodiment, the first, second and third fluid conduits 120, 122, 124 are disconnected and the cartridge 20 is pulled through the cartridge passage 42 of the second end portion 16 of the fluid concentrator 10.

In one embodiment, with the cartridge 20 disengaged from the fluid concentrator 10, the material disposed in the bore 76 of the cartridge 20 can be replaced. In another embodiment, a new cartridge 20 can replace an existing cartridge 20.

Various modifications and alterations of this disclosure will become apparent to those skilled in the art without departing from the scope and spirit of this disclosure, and it should be understood that the scope of this disclosure is not to be unduly limited to the illustrative embodiments set forth herein.

What is claimed is:

1. A fluid concentrator comprising: a main housing including: a first end portion having a first port and a second port; an oppositely disposed second end portion, the second end portion having an inlet port, the second end portion defining a cartridge passage that extends through the second end portion; a separation chamber that extends between the first and second end portions, the separation chamber being in fluid communication with the inlet port; and a cartridge removably engaged to the main housing, the cartridge defining a bore and including a first axial end portion and an oppositely disposed second axial end portion, the first axial end portion being engaged with the first end portion of the main housing when the cartridge is disposed in the main housing, a portion of the second axial end portion being disposed in the cartridge passage of the second end portion of the main housing when the cartridge is engaged to the main housing, further comprising a valve assembly in fluid communication with the separation chamber, the valve assembly defining a fluid opening that is selectively movable in the separation chamber, wherein the valve assembly includes a control handle that is selectively moveable between a first position and a second position, wherein the first position provides fluid communication between the separation chamber and the first port and the second position provides fluid communication between the first port and the cartridge.

2. The fluid concentrator of claim 1, further comprising a material disposed in the bore of the cartridge.

3. The fluid concentrator of claim 2, wherein the material is selected from the group consisting of scaffolds, graft materials, filters, cells, and combinations thereof.

4. The fluid concentrator of claim 1, wherein the first axial end portion of the cartridge includes a first port that is in selective fluid communication with the separation chamber.

5. The fluid concentrator of claim 1, wherein the cartridge defines a bore in which is disposed a filter that is adapted to filter fluid from the separation chamber.

6. The fluid concentrator of claim 1, wherein the cartridge includes a body and a first end cap disposed at the first axial end portion.

7. The fluid concentrator of claim 6, wherein the cartridge includes a second end cap disposed at the second axial end portion.

8. The fluid concentrator of claim 7, wherein the second end cap includes a gripping portion.

9. The fluid concentrator of claim 8, wherein the body of the cartridge extends outwardly from the first surface of the second end portion and the gripping portion extends outwardly from the second surface of the second end portion.

10. A fluid concentrator comprising: a main housing including: a first end portion having a first surface and an oppositely disposed second surface, the second surface defining a first fluid port, a second fluid port and a cartridge opening; an oppositely disposed second end portion, the second end portion having a first surface and an oppositely disposed second surface, the second surface defining an inlet port and a cartridge passage that extends through the first and second surfaces of the second end portion; a separation chamber that extends between the first and second end portions, the separation chamber being in fluid communication with the inlet port; a cartridge removably engaged to the main housing, the cartridge defining a bore and including a first axial end portion and an oppositely disposed second axial end portion, the first axial end portion being disposed in the cartridge opening of the first end portion of the main housing when the cartridge is engaged to the main housing, a portion of the second axial end portion being disposed in the cartridge passage of the second end portion of the main housing when the cartridge is engaged with the main housing; and a material disposed in the bore of the cartridge, further comprising a valve assembly in fluid communication with the separation chamber, the valve assembly defining a fluid opening that is selectively movable in the separation chamber, wherein the valve assembly includes a control handle that is selectively moveable between a first position and a second position, the first position providing fluid communication between the separation chamber and the first fluid port and the second position providing fluid communication between the first fluid port and the cartridge.

11. The fluid concentrator of claim 10, wherein the material is selected from the group consisting of scaffold, graft material, filter, cells, and combinations thereof.

12. The fluid concentrator of claim 10, wherein the cartridge defines a first port in fluid communication with the first fluid port of the first end portion of the main housing and a second port in fluid communication with the second fluid port of the first end portion of the main housing.

13. The fluid concentrator of claim 12, wherein the cartridge further defines a third port in fluid communication with the bore of the cartridge.

14. The fluid concentrator of claim 10, wherein the cartridge includes a body and a first end cap disposed at the first axial end portion.

15. The fluid concentrator of claim 14, wherein the cartridge includes a second end cap disposed at the second axial end portion, the second end cap including a gripping portion.

* * * * *